United States Patent [19]

Somlo

[11] Patent Number: 4,933,000
[45] Date of Patent: Jun. 12, 1990

[54] HERBICIDAL COMPOUND CONCENTRATE

[75] Inventor: Josef Somlo, Riehen, Switzerland

[73] Assignee: Ciba-Geigy Corporation, Ardsley, N.Y.

[21] Appl. No.: 228,635

[22] Filed: Aug. 4, 1988

Related U.S. Application Data

[63] Continuation-in-part of Ser. No. 105,152, Oct. 5, 1987, abandoned.

[51] Int. Cl.$^5$ .................. A01N 43/54; A01N 43/66
[52] U.S. Cl. ...................................................... 71/93
[58] Field of Search ........................... 71/DIG. 5, 93

[56] References Cited

FOREIGN PATENT DOCUMENTS 089588 of 1983 European Pat. Off. .
085376 8/1983 European Pat. Off. .
847370 9/1960 United Kingdom .
2104780 3/1983 United Kingdom .
2139893 11/1984 United Kingdom .
2184946 7/1987 United Kingdom .

Primary Examiner—David B. Springer
Attorney, Agent, or Firm—Kevin T. Mansfield

[57] ABSTRACT

There is provided a novel herbicidal compound concentrate in the form of compressed solid formulations that disintegrate in water to form a sprayable dispersion.

18 Claims, No Drawings

HERBICIDAL COMPOUND CONCENTRATE

CROSS REFERENCE TO RELATED APPLICATIONS

This is a continuation-in-part of application Ser. No. 105,152 filed Oct. 5, 1987, abandoned.

The present invention relates to a herbicidal compound concentrate in the form of compressed solid formulations which contain as active ingredient a herbicidally active sulfonyl urea and which disintegrate in water to form a sprayable dispersion.

Pesticidal compositions are, as a rule, commercially available in the form of concentrates which, on dilution with water, immediately form ready-for-use mixtures. The most common forms of such concentrates are wettable powders, water dispersible granules, emulsifiable concentrates and aqueous suspension concentrates (flowables).

A wettable powder normally comprises active substance, one or more surface-active agents and an inert solid carrier substance, for example alumina or highly dispersed silicic acid. Water dispersible granules contain, as a rule, apart from the active substance one or more dispersing agents, an inert solid carrier, such as alumina, kaolin or diatomaceous earth, and a binder, for example arabic gum, dextrin or a cellulose derivative. It has also been suggested to add an effervescing component to the granules, for example an organic acid and an alkali metal carbonate or hydrogen carbonate. Further, it has been suggested to form tablets from granules containing the effervescing component. An emulsifiable concentrate is a solution of the active substance and one or more surface-active agents in an inert solvent, for example an aromatic hydrocarbon or mineral oil. Finally, in the case of aqueous suspension concentrates, a solid active substance is suspended in water in finely divided form together with one or more surface-active agents. The ability to produce the above-mentioned basic types of concentrate depends to a large extent on the properties of the active substance.

The commercially available concentrates of active substances basically satisfy two requirements. They must be stable during storage and transport and they must be capable of conversion, before use, in a simple manner, for example by dilution with water, into a form suitable for application. Those requirements are met in various ways depending on the nature of the active substance of the various types of concentrates. For example, although wettable powders generally have sufficient stability during transport and storage, they are not easy to meter and often have a tendency to form dust against which the user has to protect himself by suitable measures, such as protective clothing and breathing masks. Water dispersible granules, as a rule, offer no problems with respect to stability during transport and storage. However, like wettable powders they often show a tendency to form dust and they are therefore not easy to handle. Moreover, the preparation of water dispersible granules is complicated since a granulating liquid, in many cases water, has to be added to the finely ground mixture of ingredients before granulation which after granulation has to be removed by drying the granules. Granules containing an effervescing agent suffer from the same disadvantages. Effervescing tablets formed from granules containing an effervescing component are only of about 5 g in weight. These tablets cannot advantageously be used in agriculture in view of their limited size. They are mostly used for the control of pests around the house where only small amounts of pesticide are applied. Emulsifiable concentrates present little difficulty with regard to stability and they are also easy to meter. The disadvantage, however, is that they contain organic solvent which on the one hand is expensive and on the other hand has an adverse effect on the toxicity of the concentrates, and the emulsions produced therefrom, on contact with the skin. Furthermore, because they contain organic solvent, emulsifiable concentrates are flammable, which constitutes a certain safety risk. Aqueous suspension concentrates, being liquids, are easy to handle and readily metered. They are free of organic solvents and the disadvantages resulting therefrom. Their stability during storage and transport is, however, satisfactory only for those active substances that, in addition to a sufficiently high melting point ($>70°$ C.), and a solubility in water of $\leqq 200$ ppm, have sufficient stability against hydrolysis. In the case of active substances having too high solubility in water, the stability of the suspension is impaired by recrystallisation processes and the enlargement of the suspended particles associated therewith. With hydrolysis-sensitive active substances, there may be marked losses in active substance, especially in the case of prolonged storage. Therefore, aqueous suspension concentrates are less suitable for the formulation of sulfonyl ureas since sulfonyl ureas possess a relatively high solubility in water and, particularly in contact with water for a prolonged period of time, a certain degree of sensibility to hydrolysis.

It is therefore the object of the present invention to provide an appropriate form of a compound concentrate for herbicidally active sulfonyl ureas which is free of the disadvantages of the known types of compound concentrates and which after addition of water is capable of forming a sprayable dispersion which is free of organic solvents.

This object is met according to the invention by providing a pesticidal compound concentrate in the form of compressed solid formulations that disintegrate in water to form a sprayable dispersion. The compound concentrate according to the invention is characterised by a content of from 5 to 75% by weight herbicidally active sulfonyl urea from 1 to 10% by weight dispersion agent from 5 to 25% by weight disintegrator comprising a water-soluble acidic substance and a carbonate or hydrogen carbonate from 1 to 35% by weight gliding and flow-regulating agent ad 100% by weight filler and binder.

Suitable sulfonyl ureas are described, for example, in the published European Patent Applications EP-A-7687, EP-A-44 808, EP-A-44 807, EP-A-84 020, EP-A-144 283, EP-A-147 365 and EP-A-158 600 and in U.S. Pat. Nos. 4,479,821, 4,599,412, 4,169,719, and 4,127,405. Especially preferred sulfonyl ureas correspond to the formula

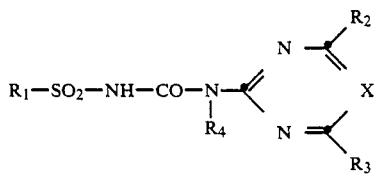

in which
R₁ represents 2-chlorophenyl, 2-methoxycarbonylphenyl, 2-ethoxycarbonylphenyl, 2-(2-methoxyethoxy)-phenyl, 2-(2-chloroethoxy)-phenyl, 2-propargyloxyphenyl, 2-methoxycarbonylthien-3-yl, 4-ethoxycarbonyl-1-methylpyrazol-5-yl, 2-methoxycarbonylbenzyl, 2-allyloxyphenyl or 2-difluoromethoxyphenyl, R₂ represents methyl, methoxy, difluoromethoxy or cyclopropyl, R₃ represents methyl, methoxy, ethoxy, difluoromethoxy or chlorine, R₄ represents hydrogen or methyl and X represents a nitrogen atom or a methine group.

There may be mentioned as especially preferred sulfonyl ureas:

N-(2-chlorophenylsulfonyl)-N'-(4-methoxy-6-methyl-1,3,5-triazin-2-yl)-urea;

N-(2-methoxycarbonylphenylsulfonyl)-N'-(4,6-bis-difluoromethoxy-1,3,5-triazin-2-yl)-urea;

N-(2-methoxycarbonylphenylsulfonyl)-N'-(4,6-dimethylpyrimidin-2-yl)-urea;

N-[2-(2-methoxyethoxy)-phenylsulfonyl]-N'-(4,6-bis-methoxy-1,3,5-triazin-2-yl)-urea;

N-[2-(2-chloroethoxy)-phenylsulfonyl]-N'-(4-methoxy-6-methyl-1,3,5-triazin-2-yl)-urea;

N-(2-methoxycarbonylthien-3-ylsulfonyl)-N'-(4-methoxy-6-methyl-1,3,5-triazin-2-yl)-urea;

N-(4-ethoxycarbonyl-1-methylpyrazol-5-yl)-N'-(4,6-bis-methoxypyrimidin-2-yl)-urea;

N-(2-methoxycarbonylbenzylsulfonyl)-N'-(4,6-bis-methoxypyrimidin-2-yl)-urea;

N-(2-ethoxycarbonylphenylsulfonyl)-N'-(4-chloro-6-methoxypyrimidin-2-yl)-urea;

N-(2-methoxycarbonylphenylsulfonyl)-N'-(4,6-bis-difluoromethoxypyrimidin-2-yl)-urea;

N-(2-methoxycarbonylphenylsulfonyl)-N'-methyl-N'-(4-methoxy-6-methyl-1,3,5-triazin-2-yl)-urea and N-(2-methoxycarbonylphenylsulfonyl)-N'-(4-methoxy-6-methyl-1,3,5-triazin-2-yl)-urea.

The content of active substance is preferably from 40 to 50% by weight.

The solid formulations according to the invention may have various shapes. Suitable shapes are, for example, cylinder, cube, small rod, egg, sphere, disc or lens. The solid formulations according to the invention are manufactured preferably in the form of tablets. The size of the solid formulations according to the invention may be varied within wide limits. The tablets generally have a diameter of from 3 to 80 mm, preferably 60 to 80 mm.

According to a preferred embodiment the present invention provides effervescent tablets having a high content of a herbicidally active sulfonyl urea. An even more preferred embodiment of the present invention comprises effervescent tablets of large size having a high content of a herbicidally active sulfonyl urea. More particularly the preferred embodiment of the present invention comprises effervescent tablets containing 40-50% by weight of a herbicidally active sulfonyl urea. According to this preferred embodiment the effervescent tablets contain 40-50% by weight of a herbicidally active sulfonyl urea, 1.5-2.5% by weight of a dispersion agent, 8-20% by weight of a solid water-soluble acidic substance, 10-25% by weight of an alkali metal or alkaline earth metal carbonate or hydrogen carbonate 1.5-3% by weight of a gliding and flow regulating agent, 0.5-3% by weight of a binder 2.5-5% by weight of water and ad 100% by weight of lactose.

Preferably, the effervescent tablets according to the invention contain from 8-12% by weight of a solid water-soluble acidic substance and 10-15% by weight of an alkali metal or alkaline earth metal carbonate or hydrogen carbonate.

Tablets having a low content of active ingredient, for example 5-30% by weight, can be produced without difficulty by thoroughly mixing the individual components in a powder mixer until homogenisation is achieved, grinding the mixture and thereafter processing the feedstock thus obtained in customary moulding devices, for example tabletting machines. However, the tablets according to the preferred embodiment of the present invention which contain 40-50% by weight of active ingredient cannot be prepared in this manner.

In connection with the preparation of effervescent tablets having a high content of a herbicidally active sulfonyl urea the following should be kept in mind. On the one hand the materials forming the feedstock, in particular those which are insoluble in water, should be ground to a particle size as small as possible in order to ensure the formation of a stable and homogeneous suspension in water after disintegration of the tablet and to avoid clogging of the spraying nozzles during application. On the other hand the difficulties encountered in the formation of tablets from a finely ground feedstock, such as poor flow characteristics of the feedstock and capping, cracking and delamination of the tablets, increase with increasing content of active substance since, as a consequence of the high content of active substance the content of the auxiliary substances which improve the flow characteristics of the feedstock and which help to avoid problems during the tabletting procedure is reduced.

According to the present invention it has been found that the aforementioned problems can be overcome by a process which comprises the use of a moist lactose which contains 8-12% by weight, preferably 9-10% by weight of water and observing an order of admixing the remaining components to the moist lactose which prevents premature reaction of the water with the effervescing agent.

According to the invention the process for the preparation of effervescing tablets having a high content of a herbicidally active sulfonyl urea comprises the steps of adding water to the lactose to adjust the water content to 8-12% by weight, conveying the moist lactose through a sieve, admixing the herbicidally active sulfonyl urea to the moist lactose and homogenising the mixture, admixing the dispersion agent, the acidic substance, the carbonate and the binder, and again homogenising the mixture, and finally admixing the gliding and flow regulating agent and forming tablets from the feedstock thus obtained.

As a rule, commercially available lactose contains about 3-5% by weight of water. However, this water content is insufficient to produce acceptable results. Therefore, the water content of the lactose has to be increased to 8-12% by weight which results in tablets containing 2.5-5% by weight of water. The feedstock can be prepared in customary mixing devices, for example in drum mixers.

The materials used for the preparation of the feedstock are ground before mixing to an appropriate particle size. It is essential that the particle size of the water-insoluble constituents, such as the herbicidally active sulfonyl urea and the gliding and flow regulating agents, does not exceed 15 μm. Preferably, the particle size of these materials is less than 15 μm. The width of the meshes of the sieve used for sieving the moist lactose is advantageously about 1-3 mm. During the formation of the tablets a pressure of 200-250 kg/cm$^2$ is applied as a rule. This results in the formation of tablets having a density of 1.1-1.2 g/cm$^3$.

With the use of the feedstock prepared as indicated above effervescent tablets having a content of 40-50% by weight of a herbicidally active sulfonyl urea can be prepared without difficulties. The feedstock shows excellent flow characteristics and tablets can be formed therefrom without capping, cracking and delamination being observed. The feedstock is also very suitable to form large size tablets having a diameter of 60-80 mm and a weight of 40-60 g which, as indicated above, represent a preferred embodiment of the present invention. The tablets show good mechanical strength and in spite of their high density and their large size disintegrate in water within about 5 minutes to form a homogeneous sprayable dispersion.

As dispersion agents which ensure the good wettability of the solid formulations according to the invention and the dispersion of the particles formed after their disintegration in water there may be used anionic and/or non-ionic surfactants. Suitable anionic surfactants are especially of sulfonic acids, and of semiesters of sulfuric acid and sulfurous acid, salts being understood as meaning the sodium, potassium, calcium, aluminium and ammonium salts, preferably the sodium salts. Especially suitable are the salts of benzene- and naphthalenesulfonic acid and the products thereof that are mono- or polyalkylated in the aromatic moiety, and also the salt of condensation products of naphthalenesulfonic acid and formaldehyde or of condensation products of naphthalenesulfonic formaldehyde or of condensation products of naphthalenesulfonic acid, phenolsulfonic acid and formaldehyde, salts of lignosulfonic acid, and salts of alkyl polyglycol ether sulfates of the formula

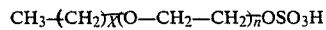

in which
X represents from 7 to 21, preferably from 11 to 17, and
n represents from 2 to 25, preferably from 18 to 22, and
also salts of semiesters of sulfuric acid with $C_{10}$-$C_{18}$-alkanols.

There may be mentioned as individual representatives of such anionic surfactants: sodium lignosulfonate, the sodium salt of the condensation product of naphthalenesulfonic acid and formaldehyde (Tamol ® SN), the sodium salt of the condensation product of naphthalenesulfonic acid, phenolsulfonic acid and formaldehyde, sodium benzenesulfonate, sodium dibutylnaphthalenesulfonate, sodium dodecylbenzenesulfonate, sodium cetyl alcohol polyglycol ether sulfate having from 2 to 20 ethylene glycol units, sodium lauryl sulfate and sodium oleic acid methyl tauride.

Suitable non-ionic surfactants are especially polyglycol ethers of $C_8$-$C_{22}$-alkanols of the formula

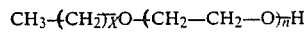

in which
X represents from 7 to 21, preferably from 9 to 17, and
n represents from 2 to 30, preferably 2 to 5 and from 18 to 23, fatty acid polyglycol esters of the formula

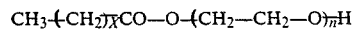

in which
X represents from 6 to 20, preferably from 8 to 16, and
n represents from 5 to 100, preferably from 8 to 30, sorbitan fatty acid esters of the formula

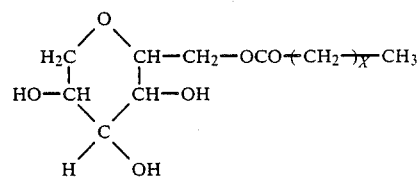

in which X represents from 6 to 20, preferably from 14 to 16, and polypropylene glycol/polyethylene glycol copolymers having a molecular weight of from 1500 to 10,000.

There may be mentioned as individual representatives of such non-ionic dispersion agents: oleyl alcohol polyglycol ether having 20 ethylene glycol units, coconut fatty alcohol polyglycol ether having 20 ethylene glycol units, lauryl alcohol polyglycol ether having 23 ethylene glycol units, cetyl alcohol polyglycol ether having 2 ethylene glycol units, stearyl alcohol polyglycol ether having 2 ethylene glycol units and sorbitan stearic acid ester.

Especially preferred surfactants are sodium lignosulfonate, sodium lauryl sulfate and sodium oleic acid methyl tauride.

The concentrates according to the invention contain preferably from 2 to 6% by weight dispersion agent.

Suitable disintegrators are generally those substances or substance mixtures which, in the presence of water, react with the evolution of gas. Suitable substances or suitable acidic substances are generally solid inorganic and organic acids, and also acidic salts of polybasic acids. Suitable acidic substances are aliphatic polycarboxylic acids, such as citric acid, tartaric acid, oxalic acid, maleic acid and adipic acid, and the acidic alkali salts of those acids. Also suitable are boric acid, acidic phosphates, such as sodium dihydrogen phosphate and acidic sulfates, such as sodium hydrogen sulfate. A preferred acid is citric acid. Suitable carbonates and hydrogen carbonates are alkali metal and alkaline earth metal carbonates, such as sodium, potassium, calcium and magnesium carbonate, and also the hydrogen carbonates of those metals. Preferred carbonates and hydrogen carbonates are alkali metal carbonates and hydrogen carbonates, particularly sodium and potassium carbonate and hydrogen carbonate.

Preferred disintegrators are mixtures of organic polycarboxylic acids and alkali carbonates. Most preferred are mixtures of citric acid and sodium carbonate or hydrogen carbonate.

There may be used as gliding and flow-regulating agents generally those substances which, in the powder mixture obtained by mixing the components, increase the glidability of the particles with respect to one another and thus ensure a good flow behaviour of the mixture, and which at the same time also increase the glidability of the compressed solid formulations so that they can be readily removed from the mould. Suitable gliding and flow-regulating agents are talcum, higher fatty acids, such as palmitic acid and stearic acid, and their magnesium, calcium, potassium and aluminium salts, $C_{14}$–$C_{18}$-alkanols, such as myristyl, cetyl and stearyl alcohol, paraffin, hydrogenated fats and oils, starch, saccharose, polyethylene glycols having a molecular weight of from 4000 to 6000, boric acid, sodium chloride and magnesium oxide. Preferred gliding and flow-regulating agents are stearic acid, magnesium stearate and talcum.

Suitable fillers and binders are inert organic and inorganic substances that on the one hand can be used as diluents and carriers for the active substance and on the other hand impart sufficient stability to the compressed solid formulation. There may be used as organic fillers and binders, for example, starch, such as potato, wheat and corn starch, dextrins, such as malto dextrin, sugars, such as lactose, glucose, saccharose, mannitol and sorbitol, cellulose, polyalkylene glycols having a molecular weight of from 4000 to 6000, sodium chloride, sodium sulfate, calcium sulfate (gypsum), dicalcium phosphate dihydrate, silicic acid, silicates, such as magnesium and aluminium silicate, and clays, such as bentonite and montmorillonite. Preferred fillers and binders are lactose, for example the product that is commercially available under the name Tablettose, and dicalcium phosphate dihydrate.

Before applying the pesticidal composition, the solid formulations according to the invention are caused to disintegrate by being stirred round in a quantity of water corresponding to the desired concentration. A homogeneous dispersion is formed that can be applied immediately by means of customary spray devices, for example knapsack sprayers or tractor sprayers.

The compound concentrates according to the invention in the form of compressed solid formulations are superior to known concentrates especially inasmuch as they are easy to handle. The compound can be metered reliably with little effort and conversion into a ready-for-use spray liquor is very easy. The burden on the environment and the user is reduced to a minimum in comparison with other solid types of formulation. In addition, less packaging material is required. The advantage of the concentrates according to the invention over conventional liquid concentrates, such as emulsifiable concentrates and aqueous suspension concentrates, is that they take up less space during transport and storage. An additional advantage over emulsifiable concentrates is that, on dilution with water, a solvent-free spray liquor is formed, while an additional advantage over aqueous suspension concentrates is that the concentrates according to the invention are suitable also for hydrolysis-sensitive substances and for substances having a solubility of $\geq 200$ ppm.

Effervescent tablets containing 40–50% by weight of a herbicidally active sulfonyl urea can be prepared according to the following general procedure:

The lactose is placed into a powder mixer and water is added through a spraying device in an amount which results in a water content of 2.5–5% by weight, preferably 3–4% by weight, calculated on the total feedstock. The moist lactose is then passed through a sieve the meshes of which are about 2 mm in width. Then the finely ground sulfonyl urea is added and the mixture is homogenised. Thereafter the dispersion agent, the acidic substance, the carbonate and the binder are added and the mixture is again homogenised. Finally, the gliding and flow regulating agent is added to complete the feedstock which subsequently can be processed in customary tabletting devices.

The composition of some typical compound concentrates according to the invention is given in the following Examples. The Examples do not, however, limit the present invention in any way.

EXAMPLE 1

10% N-[2-(2-methoxyethoxy)-phenylsulfonyl]-N'-(4,6-bis-methoxy-1,3,5-triazin-2-yl)-urea
2% sodium lignosulfonate
18% citric acid
23% sodium carbonate
3% magnesium stearate
2.5% water
ad 100% lactose

EXAMPLE 2

50% N-[2-(2-chloroethoxy)-phenylsulfonyl]-N'-(4-methoxy-6-methyl-1,3,5-triazin-2-yl)-urea
2% sodium lignosulfonate
9% citric acid
11.5% sodium carbonate
3% stearic acid powder
3% water
ad 100% lactose

EXAMPLE 3

10% N-[2-(2-methoxyethoxy)-phenylsulfonyl]-N'-(4,6-bis-methoxy-1,3,5-triazin-2-yl)-urea
2% sodium lignosulfonate
9% citric acid
11.5% sodium carbonate
33% talc
0.7% magnesium stearate
2.7% water
ad 100% lactose

EXAMPLE 4

50% N-[2-(2-chloroethoxy)-phenylsulfonyl]-N'-(4-methoxy-6-methyl-1,3,5-triazin-2-yl)-urea
2% sodium lignosulfonate
9% citric acid
11.5% sodium carbonate
3% magnesium stearate
10% dicalcium phosphate dihydrate
2.5% water
ad 100% lactose

EXAMPLE 5

42% N-[2-(2-chloroethoxy)-phenylsulfonyl]-N'-(4-methoxy-6-methyl-1,3,5-triazin-2-yl)-urea
2% sodium lignosulfonate
9% citric acid
11.5% sodium carbonate
2% cetyl alcohol polyglycol ether (EO=2)
2% stearic acid 3.5% water
ad 100% lactose

EXAMPLE 6

42% N-[2-(2-chloroethoxy)-phenylsulfonyl]-N'-(4-methoxy-6-methyl-1,3,5-triazin-2-yl)-urea
4% sodium oleic acid methyl tauride
9% citric acid
11.5% sodium carbonate
3% stearic acid
4% water
ad 100% lactose

EXAMPLE 7

42% N-[2-(2-chloroethoxy)-phenylsulfonyl]-N'-(4-methoxy-6-methyl-1,3,5-triazin-2-yl)-urea
2% sodium lignosulfonate
9% citric acid
11.5% sodium carbonate
2% propylene oxide/ethylene oxide block copolymer
3% stearic acid
3% water
ad 100% lactose

EXAMPLE 8

40% N-[2-(2-chloroethoxy)-phenylsulfonyl]-N'-(4-methoxy-6-methyl-1,3,5-triazin-2-yl)-urea
2% sodium lignosulfonate
9% citric acid
11.5% sodium carbonate
2% stearic acid
1% malto-dextrin
3.5% water
ad 100% lactose

EXAMPLE 9

40% N-(2-methoxycarbonylphenylsulfonyl)-N'-(4,6-bis-difluoromethoxypyrimidin-2-yl)-urea
2% sodium lignosulfonate
9% citric acid
11.5% sodium carbonate
2% stearic acid
1% malto-dextrin
3.5% water
ad 100% lactose

EXAMPLE 10

40% N-(2-methoxycarbonylphenylsulfonyl)-N'-(4,6-bis-difluoromethoxypyrimidin-2-yl)-urea
2% sodium lignosulfonate
9% citric acid
11.5% sodium carbonate
2% stearic acid
1% malto-dextrin
1.6% water
ad 100% lactose

I claim:

1. A herbicidal compound concentrate in the form of tablets that disintegrate in water to form a sprayable dispersion, which contain
   40-50% by weight of a herbicidally active sulfonyl urea,
   1.5-2.5% by weight of a dispersion agent,
   8-20% by weight of a solid water-soluble acidic substance,
   10-25% by weight of an alkali metal or alkaline earth metal carbonate or hydrogen carbonate,
   1.5-3% by weight of a gliding and flow regulating agent,
   0.5-3% by weight of a binder and
   ad 100% by weight of lactose containing 8-12% by weight of water.

2. Herbicidal compound concentrate according to claim 1, characterised in that it contains from 8-12% by weight of a solid water-soluble acidic substance and 10-25% by weight of an alkali metal or alkaline earth metal carbonate or hydrogen carbonate.

3. Herbicidal compound concentrate according to claim 1, characterised in that it contains as active substance a herbicidally active sulfonyl urea of the formula

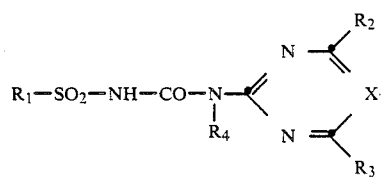

in which
R$_1$ represents 2-chlorophenyl, 2-methoxycarbonylphenyl, 2-ethoxycarbonylphenyl, 2-(2-methoxyethoxy)-phenyl, 2-(2-chloroethoxy)-phenyl, 2-propargyloxyphenyl, 2-methoxycarbonylthien-3-yl, 4-ethoxycarbonyl-1-methylpyrazol-5-yl, 2-methoxycarbonylbenzyl, 2-allyloxyphenyl or 2-difluoromethoxyphenyl,
R$_2$ represents methyl, methoxy, difluoromethoxy or cyclopropyl,
R$_3$ represents methyl, methoxy, ethoxy, difluoromethoxy or chlorine,
R$_4$ represents hydrogen or methyl and
X represents a nitrogen atom or a methine group.

4. A herbicidal compound concentrate according to claim 3, characterised in that it contains as active substance a herbicidally active sulfonyl urea selected from the group;
N-(2-chlorophenylsulfonyl)-N'-(4-methoxy-6-methyl-1,3,5-triazin-2-yl)-urea;
N-(2-methoxycarbonylphenylsulfonyl)-N'-(4,6-bis-difluoromethoxy-1,3,5-triazin-2-yl)-urea;
N-(2-methoxycarbonylphenylsulfonyl)-N'-(4,6-dimethylpyrimidin-2-yl)-urea,
N-[2-(2-methoxyethoxy)-phenylsulfonyl]-N'-(4,6-bis-methoxy-1,3,5-triazin-2-yl)-urea;
N-[2-(2-chloroethoxy)-phenylsulfonyl]-N'-(4-methoxy-6-methyl-1,3,5-triazin-2-yl)-urea;
N-(2-methoxycarbonylthien-3-ylsulfonyl)-N'-(4-methoxy-6-methyl-1,3,5-triazin-2-yl)-urea;
N-(4-ethoxycarbonyl-1-methylpyrazol-5-yl)-N'-(4,6-bis-methoxypyrimidin-2-yl)-urea;
N-(2-methoxycarbonylbenzylsulfonyl)-N'-(4,6-bis-methoxypyrimidin-2-yl)-urea;
N-(2-ethoxycarbonylphenylsulfonyl)-N'-(4-chloro-6-methoxypyrimidin-2-yl)-urea;
N-(2-methoxycarbonylphenylsulfonyl)-N'-(4,6-bis-difluoromethoxypyrimidin-2-yl)-urea;
N-(2-methoxycarbonylphenylsulfonyl)-N'-methyl-N'-(4-methoxy-6-methyl-1,3,5-triazin-2-yl)-urea and
N-(2-methoxycarbonylphenylsulfonyl)-N'-(4-methoxy-6-methyl-1,3,5-triazin-2-yl)-urea.

5. A herbicidal compound concentrate according to claim 1, characterised in that it contains as dispersion agent an anionic and/or non-ionic surfactant.

6. A herbicidal compound concentrate according to claim 5, characterised in that it contains as dispersion agent sodium lignosulfonate, sodium lauryl sulfate or sodium oleic acid methyl tauride.

7. A herbicidal compound concentrate according to claim 6, characterised in that it contains as solid acidic substance an inorganic or organic acid or an acidic salt of a polybasic acid.

8. A herbicidal compound concentrate according to claim 6, characterised in that it contains as acidic substance citric acid, tartaric acid, oxalic acid, maleic acid or adipic acid or an acidic alkali salt of one of those acids.

9. A herbicidal compound concentrate according to claim 8, characterised in that it contains as acidic substance citric acid.

10. A herbicidal compound concentrate according to claim 1, characterised in that it contains sodium or potassium carbonate or hydrogen carbonate.

11. A herbicidal compound concentrate according to claim 1, characterised in that it contains as gliding and flow-regulating agent talcum, a higher fatty acid or the magnesium, calcium, potassium or aluminium salt thereof, a $C_{14}$–$C_{18}$-alkanol, paraffin, a hydrogenated fat or a hydrogenated oil, starch, saccharose, polyethylene glycols having a molecular weight of from 4000 to 6000, boric acid, sodium chloride or magnesium oxide.

12. A herbicidal compound concentrate according to claim 11, characterised in that it contains as gliding and flow-regulating agent palmitic acid, stearic acid, or a magnesium, calcium, potassium or aluminium salt of one of those acids, myristyl alcohol, cetyl alcohol or stearyl alcohol.

13. A herbicidal compound concentrate according to claim 12, characterised in that it contains as gliding and flow-regulating agent stearic acid, magnesium stearate or talcum.

14. A herbicidal compound concentrate according to claim 1, characterised in that it contains dextrin as binder.

15. A herbicidal compound concentrate according to claim 1, characterised in that it contains malto-dextrin as binder.

16. A herbicidal compound concentrate according to claim 1 which comprises effervescing tablets having a diameter of 60–80 mm and a weight of 40–60 g.

17. Process for the preparation of effervescing tablets containing
40–50% by weight of a herbicidally active sulfonyl urea,
1.5–2.5% by weight of a dispersion agent,
8–12% by weight of a solid water-soluble acidic substance,
10–15% by weight of an alkali metal or alkaline earth metal carbonate or hydrogen carbonate
1.5–3% by weight of a gliding and flow regulating agent,
0.5–3% by weight of a binder
2.5–5% by weight of water and
ad 100% by weight of lactose,
which process comprises the steps of
(a) adding water to the lactose to adjust the water content to 8–12% by weight,
(b) conveying the moist lactose through a sieve,
(c) admixing the herbicidally active sulfonyl urea to the moist lactose and homogenizing the mixture,
(d) admixing the dispersion agent, the acidic substance, the carbonate and the binder, and again homogenising the mixture, and finally
(e) admixing the gliding and flow regulating agent and
(f) forming tablets from the feedstock thus obtained.

18. A herbicidal compound concentrate according to claim 1, wherein the lactose contains 9–10% by weight of water.

* * * * *